United States Patent
Memmolo et al.

(10) Patent No.: US 11,918,434 B2
(45) Date of Patent: *Mar. 5, 2024

(54) DENTAL IMPLANT

(71) Applicant: Nobel Biocare Services AG, Kloten (CH)

(72) Inventors: Marcello Memmolo, Reinach (CH); Jan Hall, Gothenburg (SE); Emmanuel De Haller, Neftenbach (CH)

(73) Assignee: Nobel Biocare Services AG, Kloten (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/806,425

(22) Filed: Jun. 10, 2022

(65) Prior Publication Data

US 2022/0378554 A1   Dec. 1, 2022

Related U.S. Application Data

(63) Continuation of application No. 15/535,890, filed as application No. PCT/EP2015/079603 on Dec. 14, 2015, now Pat. No. 11,357,600.

(30) Foreign Application Priority Data

Dec. 16, 2014  (EP) ..................... 14198377

(51) Int. Cl.
*A61C 8/00*  (2006.01)
*A61K 6/69*  (2020.01)
(Continued)

(52) U.S. Cl.
CPC .......... *A61C 8/0015* (2013.01); *A61C 8/0013* (2013.01); *A61K 6/69* (2020.01); *A61K 6/816* (2020.01); *A61K 6/84* (2020.01)

(58) Field of Classification Search
CPC ... A61C 8/0015; A61C 8/0013; A61C 8/0012; A61K 6/816; A61K 6/69; A61K 6/84;
(Continued)

(56) References Cited

U.S. PATENT DOCUMENTS

| 4,195,409 A * | 4/1980 | Child ................ A61C 8/0012 |
| | | 433/175 |
| 4,261,063 A | 4/1981 | Blanquaert |

(Continued)

FOREIGN PATENT DOCUMENTS

| CA | 2 442 582 | 10/2002 |
| CN | 1392799 A | 1/2003 |

(Continued)

OTHER PUBLICATIONS

TiUnite—Die einzgartige Titanoxidoberfläche, jetz neu im Branemark-System, Nobel Biocare Catalog, cited on Aug. 9, 2011 in an Opposition against European Patent EP 1696816 (European Application No. EP 04820332.7), 8 pages.

(Continued)

*Primary Examiner* — Ralph A Lewis
*Assistant Examiner* — Mirayda A Aponte
(74) *Attorney, Agent, or Firm* — Knobbe Martens Olson & Bear LLP

(57) ABSTRACT

The present disclosure provides a dental implant configured to be inserted in a hole in jaw bone and to be at least partially situated in the bone tissue when implanted and includes: a coronal region, an apical region, a longitudinal axis extending from the coronal region of the dental implant to the apical region of the dental implant; an implant surface configured to form an interface between an implant material and the oral environment/surrounding tissue and a surface layer formed on at least part of the implant surface, the surface layer including crystalline titanium oxide in the (Continued)

anatase phase and wherein the surface area roughness Sa and the pore size of the implant surface on which said surface layer is formed increase from the coronal region toward the apical region of the dental implant along the longitudinal axis.

20 Claims, 1 Drawing Sheet

(51) Int. Cl.
*A61K 6/816* (2020.01)
*A61K 6/84* (2020.01)

(58) Field of Classification Search
CPC . A61K 6/802; A61K 6/80; A61K 6/60; A61D 6/067; A61D 6/0235; A61D 6/04; A61D 6/816; A61D 6/69; A61D 6/84; A61D 6/802; A61D 6/80
USPC .................................... 433/173–176, 201.1
See application file for complete search history.

(56) References Cited

U.S. PATENT DOCUMENTS

| | | | |
|---|---|---|---|
| 4,262,063 A | 4/1981 | Kudo et al. |
| 4,330,891 A | 5/1982 | Branemark et al. |
| 5,108,399 A | 4/1992 | Eitenmuller |
| 5,152,794 A | 10/1992 | Davidson |
| 5,180,394 A | 1/1993 | Davidson |
| 5,282,861 A | 2/1994 | Kaplan |
| 5,350,302 A | 9/1994 | Marlin |
| 5,354,390 A | 10/1994 | Haszmann |
| 5,489,306 A | 2/1996 | Gorski |
| 5,697,779 A | 12/1997 | Sachdeva et al. |
| 5,866,271 A | 2/1999 | Stueber et al. |
| 6,103,363 A | 8/2000 | Boire et al. |
| 6,174,167 B1 | 1/2001 | Wohrle |
| 6,183,255 B1 | 2/2001 | Oshida |
| 6,220,861 B1 | 4/2001 | Kwon et al. |
| 6,521,246 B2 | 2/2003 | Sapieszko et al. |
| 6,527,554 B2 | 3/2003 | Hurson et al. |
| 6,702,855 B1 | 3/2004 | Steinemann et al. |
| 6,951,463 B2 | 10/2005 | Masuhara et al. |
| 7,048,541 B2 | 5/2006 | Hall et al. |
| 7,291,178 B2 | 11/2007 | Sul |
| 7,410,502 B2 | 8/2008 | Ellingsen et al. |
| 7,445,640 B2 | 11/2008 | Despres, III et al. |
| 7,708,558 B1 | 5/2010 | Hall |
| 7,771,774 B2 | 8/2010 | Berckmans, III et al. |
| 7,951,285 B2 | 5/2011 | Zipprish |
| 7,972,648 B2 | 7/2011 | Berckmans, III et al. |
| 7,998,568 B2 | 8/2011 | Raja et al. |
| 8,029,283 B2 | 10/2011 | Schwarz et al. |
| 8,043,090 B1 | 10/2011 | Lyren |
| 8,057,843 B2 | 11/2011 | Schlottig et al. |
| 8,110,242 B2 | 2/2012 | Hawkins et al. |
| 8,241,036 B2 | 8/2012 | Breitenstein et al. |
| 8,297,974 B1 | 10/2012 | Lyren |
| 8,377,106 B2 | 2/2013 | Branemark et al. |
| 8,399,008 B2 | 3/2013 | Webster et al. |
| 8,408,906 B2 | 4/2013 | de Wild et al. |
| 8,414,908 B2 | 4/2013 | Jin et al. |
| 8,684,734 B1 | 4/2014 | Lyren |
| 8,764,444 B2 | 7/2014 | Hansson |
| 8,789,693 B2 | 7/2014 | Schlottig et al. |
| 8,821,586 B2 | 9/2014 | Bjursten et al. |
| 8,876,910 B2 | 11/2014 | Gilbert et al. |
| 8,920,866 B2 | 12/2014 | Schlottig et al. |
| 9,034,201 B2 | 5/2015 | Mayfield et al. |
| 9,131,995 B2 | 9/2015 | Mayfield et al. |
| 9,168,110 B2 | 10/2015 | Towse et al. |
| 9,242,029 B2 | 1/2016 | Jennissen et al. |
| 9,283,056 B2 | 3/2016 | Mayfield et al. |
| 9,327,056 B2 | 5/2016 | Bandyopadhyay et al. |
| 9,539,067 B2 | 1/2017 | Berckmans, III et al. |
| 9,642,680 B2 | 5/2017 | Berner |
| 9,642,708 B2 | 5/2017 | Fredriksson et al. |
| 9,668,889 B2 | 6/2017 | Holt et al. |
| 9,724,450 B2 | 8/2017 | Opie et al. |
| 9,757,210 B2 | 9/2017 | Axen et al. |
| 9,757,212 B2 | 9/2017 | Mayfield et al. |
| 9,763,751 B2 | 9/2017 | Berckmans, III et al. |
| 9,795,712 B2 | 10/2017 | Opie et al. |
| 9,931,184 B2 | 4/2018 | Hall |
| 9,993,319 B2 | 6/2018 | Berner et al. |
| 10,040,727 B2 | 8/2018 | Berner |
| 11,357,600 B2 * | 6/2022 | Memmolo ............. A61K 6/816 |
| 2001/0002994 A1 | 6/2001 | Masuhara et al. |
| 2003/0158554 A1 | 8/2003 | Hall |
| 2004/0121286 A1 | 6/2004 | Aravena et al. |
| 2004/0236338 A1 | 11/2004 | Hall |
| 2004/0267376 A1 | 12/2004 | Suzuki et al. |
| 2005/0019365 A1 | 1/2005 | Frauchiger et al. |
| 2005/0103639 A1 | 5/2005 | Lu et al. |
| 2005/0113834 A1 | 5/2005 | Breitenstein et al. |
| 2005/0175658 A1 | 8/2005 | DiMauro et al. |
| 2006/0149391 A1 | 7/2006 | Opie et al. |
| 2006/0229715 A1 | 10/2006 | Istephanous et al. |
| 2007/0202466 A1 | 8/2007 | Schwarz et al. |
| 2007/0275350 A1 | 11/2007 | Hall |
| 2008/0004691 A1 | 1/2008 | Weber et al. |
| 2008/0097618 A1 | 4/2008 | Baker et al. |
| 2008/0213726 A1 | 9/2008 | Schlottig et al. |
| 2008/0220394 A1 | 9/2008 | Berckmans et al. |
| 2008/0269910 A1 | 10/2008 | Ellingsen et al. |
| 2009/0011384 A1 | 1/2009 | Collins et al. |
| 2009/0132048 A1 | 5/2009 | Denzer |
| 2009/0220913 A1 | 9/2009 | Geis-Gerstorfer |
| 2010/0112519 A1 | 5/2010 | Hall et al. |
| 2010/0168854 A1 | 7/2010 | Luers et al. |
| 2011/0233169 A1 | 9/2011 | Mayfield et al. |
| 2011/0311946 A1 | 12/2011 | Sailer et al. |
| 2012/0021008 A1 | 1/2012 | De Bruijn et al. |
| 2012/0040102 A1 | 2/2012 | Meredith |
| 2012/0189833 A1 | 7/2012 | Suchanek et al. |
| 2012/0288699 A1 | 11/2012 | Ahlberg et al. |
| 2013/0045360 A1 | 2/2013 | Ibacache et al. |
| 2013/0233717 A1 | 9/2013 | Disegi |
| 2014/0011161 A1 | 1/2014 | Berckmans, III et al. |
| 2014/0141201 A1 | 5/2014 | Berner et al. |
| 2014/0170600 A1 | 6/2014 | Koncewicz |
| 2014/0174939 A1 | 6/2014 | Hal |
| 2014/0178639 A1 | 6/2014 | Berner |
| 2014/0329052 A1 | 11/2014 | Gittens Ibacache et al. |
| 2014/0342314 A1 | 11/2014 | Chamblee |
| 2014/0342316 A1 | 11/2014 | Berner et al. |
| 2014/0343687 A1 | 11/2014 | Jennissen |
| 2015/0037758 A1 | 2/2015 | Tatum, Jr. et al. |
| 2015/0056573 A1 | 2/2015 | Collins et al. |
| 2015/0086943 A1 | 3/2015 | Schwarz et al. |
| 2015/0209480 A1 | 7/2015 | Byon et al. |
| 2015/0245899 A1 | 9/2015 | Lyngstadaas et al. |
| 2015/0289951 A1 | 10/2015 | Mayfield et al. |
| 2015/0351874 A1 | 12/2015 | Axén et al. |
| 2016/0030140 A1 | 2/2016 | Towse et al. |
| 2016/0045289 A1 | 2/2016 | Berckmans, III et al. |
| 2016/0058920 A1 | 3/2016 | Ha et al. |
| 2016/0120625 A1 | 5/2016 | Berner |
| 2016/0120626 A1 | 5/2016 | Berner |
| 2016/0136336 A1 | 5/2016 | Jennissen et al. |
| 2016/0228992 A1 | 8/2016 | Bandyopadhyay et al. |
| 2016/0278885 A1 | 9/2016 | Kirsten et al. |
| 2017/0001920 A1 | 1/2017 | Berner |
| 2017/0079752 A1 | 3/2017 | Hal |
| 2017/0112962 A1 | 4/2017 | Storey et al. |
| 2017/0196662 A1 | 7/2017 | Perler et al. |
| 2017/0218522 A1 | 8/2017 | Baytekin-Gerngross et al. |
| 2017/0224458 A1 | 8/2017 | Martin et al. |
| 2017/0258556 A1 | 9/2017 | Watanabe et al. |
| 2018/0153660 A1 | 6/2018 | Berner |
| 2019/0046299 A1 | 2/2019 | Kim |
| 2019/0117344 A1 | 4/2019 | Schwarz et al. |

(56) References Cited

U.S. PATENT DOCUMENTS

| | | |
|---|---|---|
| 2022/0087784 A1 | 3/2022 | Gilgenbach Blume et al. |
| 2022/0192794 A1 | 6/2022 | Gilgenbach Blume et al. |
| 2023/0070222 A1 | 3/2023 | Nagel et al. |

FOREIGN PATENT DOCUMENTS

| | | |
|---|---|---|
| CN | 1817319 A | 8/2006 |
| CN | 103736148 A | 4/2014 |
| DE | 3445848 A1 | 6/1986 |
| DE | 4311772 A1 | 10/1993 |
| DE | 4216122 A1 | 11/1993 |
| DE | 10 2006 021968 A1 | 11/2007 |
| EP | 0 388 576 A1 | 9/1990 |
| EP | 0 806 211 A1 | 11/1997 |
| EP | 1 191 901 B1 | 4/2005 |
| EP | 1 527 790 A1 | 5/2005 |
| EP | 1 652 963 A1 | 5/2006 |
| EP | 1 825 830 A1 | 8/2007 |
| EP | 1 847 278 A1 | 10/2007 |
| EP | 1 492 579 B1 | 9/2008 |
| EP | 1 196 110 B1 | 1/2009 |
| EP | 1 534 168 B1 | 6/2010 |
| EP | 1 980 276 B1 | 3/2011 |
| EP | 2 292 178 A1 | 3/2011 |
| EP | 1 397 168 B1 | 5/2011 |
| EP | 1 825 829 B1 | 8/2011 |
| EP | 2 161 000 B1 | 8/2011 |
| EP | 1 534 175 B1 | 10/2011 |
| EP | 2 160 998 B1 | 4/2012 |
| EP | 2 436 336 A1 | 4/2012 |
| EP | 2 319 461 B1 | 9/2012 |
| EP | 2 289 460 B1 | 4/2013 |
| EP | 2 398 518 B1 | 4/2013 |
| EP | 1 274 470 B1 | 6/2013 |
| EP | 1 696 816 B2 | 10/2013 |
| EP | 2 537 485 B1 | 5/2015 |
| EP | 1 982 671 B1 | 3/2016 |
| EP | 3 011 980 A1 | 4/2016 |
| EP | 1 622 656 B1 | 7/2016 |
| EP | 3 195 825 A1 | 7/2017 |
| EP | 3 854 342 | 7/2021 |
| JP | 07-328037 A | 12/1995 |
| JP | 11-033106 | 2/1999 |
| JP | 2000-116673 | 4/2000 |
| JP | 2002-102330 | 4/2002 |
| JP | 5037136 B2 | 9/2012 |
| JP | 5523709 B2 | 6/2014 |
| JP | 2014-204867 | 10/2014 |
| SE | 514202 | 1/2001 |
| SE | 516282 | 12/2001 |
| WO | WO 00/072776 A1 | 12/2000 |
| WO | WO 00/072777 A1 | 12/2000 |
| WO | WO 01/076653 A1 | 10/2001 |
| WO | WO 02/078759 A1 | 10/2002 |
| WO | WO 02/096475 A1 | 12/2002 |
| WO | WO 03/003937 A1 | 1/2003 |
| WO | WO 03/063925 A1 | 8/2003 |
| WO | WO 03/086495 A1 | 10/2003 |
| WO | WO 2004/008984 A1 | 1/2004 |
| WO | WO 2004/091424 A1 | 10/2004 |
| WO | WO 2005/055858 A1 | 6/2005 |
| WO | WO 2005/055859 A1 | 6/2005 |
| WO | WO 2005/055860 A1 | 6/2005 |
| WO | WO 2006/004686 A2 | 1/2006 |
| WO | WO 2007/059038 A2 | 5/2007 |
| WO | WO 2007/091155 A1 | 8/2007 |
| WO | WO 2007/118734 A1 | 10/2007 |
| WO | WO 2010/094968 A2 | 8/2010 |
| WO | WO 2011/066098 A1 | 6/2011 |
| WO | WO 2013/056844 A1 | 4/2013 |
| WO | WO 2014/195025 A2 | 12/2014 |
| WO | WO 2014/195027 A2 | 12/2014 |
| WO | WO 2015/044401 A2 | 4/2015 |
| WO | WO 2015/132325 A1 | 9/2015 |
| WO | WO 2015/145450 A1 | 10/2015 |
| WO | WO 2016/009372 A1 | 1/2016 |
| WO | WO 2016/042515 A1 | 3/2016 |
| WO | WO 2016/062882 A1 | 4/2016 |
| WO | WO 2016/118038 A1 | 7/2016 |
| WO | WO 2016/185186 A1 | 11/2016 |
| WO | WO 2016/189099 A1 | 12/2016 |
| WO | WO 2017/009500 A1 | 1/2017 |
| WO | WO 2017/075364 A1 | 5/2017 |
| WO | WO 2017/210758 A1 | 12/2017 |
| WO | WO 2018/011604 A2 | 1/2018 |

OTHER PUBLICATIONS

Branemark System, STERI-OSS, Replace, PROCERA, GORE—Nobel Biocare Catalog, dated Aug. 9, 2011, 10 pages.
All in One—Nobel Biocare Catalog, 2001, 10 pages.
Replace—TiUnite—Nobel Biocare Catalog, 2001, 6 pages.
Replace Introduces TiUnite, A Unique Oxidized Titanium Surface—Nobel Biocare Catalog, 2001, 10 pages.
Response to USPTO (Remarks in Amendment for U.S. Appl. No. 10/582,468) dated Dec. 27, 2011 in 4 pages.
Reply from USPTO (Office Action of U.S. Appl. No. 10/582,468) dated Jan. 31, 2012 in 8 pages.
Battiston, G.A. et al. "Dental Implants of Complex Form Coated by Nanostructured TiO2 Thin Films via MOCVD," Materials Science Forum, vol. 352, pp. 151-158, 2000.
Born, R. et al. "Surface analysis of titanium based biomaterials," J. Anal. Chem., 361: 697-700, 1998.
Del Curto, B. et al., "Decreased bacterial adhesion to surface-treated titanium," The International Journal of Artificial Organs, vol. 28, No. 7, pp. 718-730, 2005.
Expressing Universality, dated Sep. 8, 2012 in 8 pages.
Hall, J. et al., "Properties of a new porous oxide surface on titanium implants," Applied Osseointegration Research, vol. 1, pp. 5-8, 2000.
Hanaor et al. "Review of the anatase to rutile phase transformation," Journal of Material Science, vol. 46, pp. 855-874, 2011.
Ignatov, V. "Biocompartible Coatings on Titanium Implants," Science and Technology, pp. 197-201, Jun. 28, 2003.
Kokubo, T. et al. "Novel bioactive materials with different mechanical properties," vol. 24, No. 13; pp. 2-16, Jun. 2003.
Miyazaki, T. et al., "Auger Electron Spectroscopic Studies of Titanium Implants Treated by Several Finishing Porcedures," J. Showa Univ. Dent. Soc. 11:322-326, 1991.
Smith, G.C. et al., "Soft tissue response to titanium dioxide nanotube modified implants," Acta Biomaterialia 7, 3209-3215, 2011.
Rossi, S. et al., "Comparison between sol-gel-derived anatase- and rutile-structured TiO2 coatings in soft-tissue environment," J. Biomedical Materials Research Part A, pp. 965-974, Mar. 2, 2007.
Ruano, R. et al., "Effect of a Ceramic and a Non-Ceramic Hydroxyapatite on Cell Growth and Procollagen Synthesis of Cultured Human Gingival Fibroblasts," J. Periodontol., vol. 71, No. 4, pp. 540-545, Apr. 2000.
Schroeder, A. et al. "Orale Implantologic," Georg Thieme Verlag Stuttgart 1994, in 5 pages.
Sul, YT et al., "Resonance frequency and removal torque analysis of implants with turned and anodized surface oxides," Clinical Oral Implants Research, 13, pp. 252-259, 2002.
Zhao, Jingmei, "Oral titanium implant surface modification and its biological properties", China Master's Theses Full-text Database, Engineering Technology, series I, B022-123, published on Jul. 15, 2013.
Wennerberg et al., "Current knowledge about the hydrophilic and nanostructured SLActive surface," Clinical, Cosmetic and Investigational Dentistry, Dovepress, pp. 59-67, Sep. 5, 2011.
Wennerberg et al., "On Implant Surfaces: A Review of Current Knowledge and Opinions," International J. of Oral & Maxillofacial Implants, vol. 25, No. 1, pp. 63-74, Jan.-Feb. 2010.
Bjursten et al., "Titanium dioxide nanotubes enhance bone bonding in vivo," J. of Biomedical Materials Research Part A, Wiley InterScience, pp. 1218-1224, Apr. 2, 2009.
Zhao et al., "The influence of hierarchical hybrid micro/nano-textured titanium surface with titania nanotubes on osteoblast functions," Biomaterials 31, pp. 5072-5082, Apr. 2, 2010.

(56) References Cited

OTHER PUBLICATIONS

Gao et al., "Micro/Nanostructural Porous Surface on Titanium and Bioactivity," J. of Biomedical Materials Research Part B: Applied Biomaterials, Wiley InterScience, pp. 335-341, Oct. 6, 2008.
Liu et al., "Surface modification of titanium, titanium alloys, and related materials for biomedical applications," Materials Science and Engineering R 47 pp. 49-121, 2004.
Gong et al., "Titanium oxide nanotube arrays prepared by anodic oxidation," J. Mater. Res., vol. 16, No. 12, pp. 3331-3334, Dec. 2001.
Parkhutik et al., "Theoretical modelling of porous oxide growth on aluminium," J. Phys. D: Appl. Phys. 25, pp. 1258-1263, 1992.
Kim et al., "Electrochemical surface modification of titanium in dentistry," Dental Materials Journal 28(1), 20-36, 2009.
Sul, Young-Taeg, "The significance of the surface properties of oxidized titanium to the bone response: special emphasis on potential biochemical bonding of oxidized titanium implant," Biomaterials 24, pp. 3893-3907, 2003.
Lüers et al., "Protecting ultra- and hyperhydrophilic implant surfaces in dry state from loss of wettability", Current Directions in Biomedical Engineering 2016; vol. 2, No. 1, pp. 557-560, Sep. 30, 2016.
Rupp et al., "Enhancing surface free energy and hydrophilicity through chemical modification of microstructured titanium implant surfaces," J. Biomed Mater Res A. 2006, vol. 76, pp. 323-334.
International Search Report for Application No. PCT/EP2015/079603 dated Mar. 14, 2016 in 4 pages.
International Search Report for Application No. PCT/EP2015/054573 filed Mar. 5, 2015 (Publication WO 2015/132325 published Sep. 11, 2015) dated Apr. 24, 2015 in 4 pages.
Jaeggi C. et al., "Anodic thin films on titanium used as masks for surface micropatterning of biomedical devices," Surface and Coatings Technology, Elsevier, Amsterdam, NL, vol. 200, No. 5-6, pp. 1913-1919, Nov. 21, 2005.
Chen Z. X. et al., "Surface characteristics and in vitro biocompatibility of titanium anodized in a phosphoric acid solution at different voltages," Biomedical Materials, Institute of Physics Publishing, Bristol, GB, vol. 4, No. 6, p. 65003, Dec. 1, 2009.
International Search Report for PCT Application No. PCT/SE2004/001806 filed Dec. 6, 2004 (Publication WO 2005/055860 published Jun. 23, 2005) dated Apr. 6, 2005 in 2 pages.
International Preliminary Report on Patentability for PCT Application No. PCT/SE2004/001806 filed Dec. 6, 2004 (Publication WO 2005/055860 published Jun. 23, 2005) dated Mar. 20, 2006 in 4 pages.
Summons to Attend Oral Proceedings Pursuant to Rule 115(1) EPC in European Application No. EP 04820332.7, dated May 2, 2012 in 12 pages.
Grounds for the Decision in European Application No. EP 04820332.7, dated Feb. 1, 2013 in 43 pages.
TiUnite, Website nobelbiocare.com, dated Jul. 20, 2011 in 1 page.
Medienmitteilung—Nobel Bioacare unterzeichnet mit Wyeth eine exklusive Lizenzvereinbarung fur die Nutzung des rhBMP-2-Proteins fur Dentalimplantate, Jun. 9, 2005, 2 pages.

\* cited by examiner

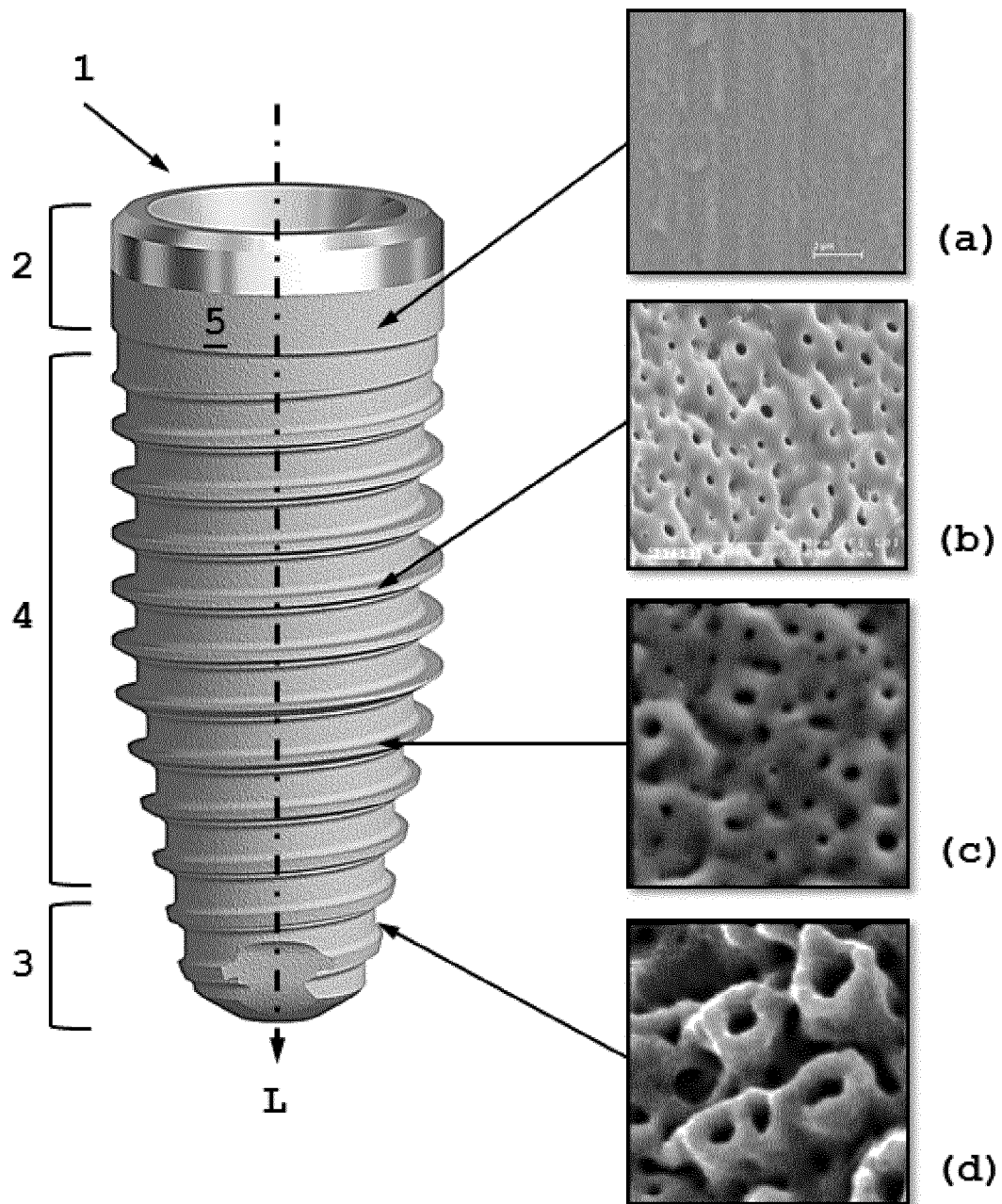

DENTAL IMPLANT

CROSS-REFERENCE TO RELATED APPLICATIONS

This application is a continuation of U.S. application Ser. No. 15/535,890, filed Jun. 14, 2017, which is a national stage application under 35 U.S.C. § 371 of International Application No. PCT/EP2015/079603, filed on Dec. 14, 2015, which published in English as WO 2016/096734 A1 on Jun. 23, 2016 and which claims priority benefit of EP Patent Application No. 14198377.5 filed on Dec. 16, 2014.

BACKGROUND

Technical Field

The present invention relates to a dental implant that is configured to be inserted in a hole in jaw bone.

Description of the Related Art

For the past 50 years dental implants have been successfully used to replace lost or missing teeth. One of the overriding challenges in implant dentistry is to modify the properties of soft tissue adhering surfaces to promote optimal soft-tissue adherence at the same time as minimizing bacterial adhesion and bio film formation and allowing the maintenance of good oral hygiene. In order to minimize the risk of microbial colonization on e.g. the spacer surface, the coronal region of the implant or any device in contact with soft tissue, it is believed that the surfaces shall be smooth with structures that limit bacteria growth. Therefore, it is common to manufacture the coronal implant system parts by machining, such as milling and/or turning, which results in smooth surfaces with structures in the sub- or low micrometer range. Implants and spacer sleeves with such surfaces have been used successfully for decades.

In most cases, soft tissue integration is good and bacteria growth is limited on the machined structures and peri-implant infections can be avoided. However, they do occur, and a few percent of all patients rehabilitated with dental implants experience complications due to peri-implant infections. It is therefore desired to continue to reduce the risk of peri-implant infection while maintaining good soft tissue integration.

One of the factors thought to be important in preventing peri-implant infections is the formation of a tight soft-tissue seal around the neck of the implant.

On placement of an implant into the jaw bone, exposed surfaces of a spacer and in some cases also parts of the neck of the implant, which emerge through the mucosa, immediately become covered with an acquired pellicle of proteins derived from the surrounding environment. Adsorbed proteins provide a range of binding sites for oral bacteria to attach and initiate the development of a biofilm. Once colonization has been initiated, the primary colonizers present new sites for adhesion of secondary colonizers and biofilm formation are thereby initiated. Continuous undisturbed growth of such biofilms can result in gradual colonization of the whole spacer surface including the most coronal implant area. In some cases, extensive biofilm growth may result in an infection and an inflammatory host response that result in tissue breakdown. Such a condition is usually referred to as "peri-implantitis", and it may lead to implant failure.

Peri-implantitis is an inflammatory process that affects the soft and hard tissues surrounding an osseointegrated implant, and this process is accompanied by specific pathogenic microbes which are identified in the peri-implant pockets. The aethiology of peri-implantitis is multifactorial and up to now not really well understood. It is influenced by the microbial composition in the oral cavity, the genetic disposition and/or immune status of the patient, the practiced oral hygiene, and the physical condition and age of the patient. Microbial plaque accumulation and severe bacterial infection may lead as a consequence to rapid bone loss associated with bleeding and suppuration. This condition has been described as the breakdown of bone tissue as a response to inflammation resulting from bacterial infection surrounding an endosseous dental implant.

Various implant structures of fixtures, spacers and prosthetic components have been presented over the years. In addition, various substances and compositions have been proposed for being used as coatings on substrates, such as to form an implant surface. However, as will be recognized after having read the technical background of the present application, the human body is a highly advanced and complex environment and it is not an obvious task how to design an implant structure to overcome the described issues.

One way to treat implants that have been used for and shown excellent result for osseointegration in bone is the TiUnite® surface. The surface treatment is obtained by means of anodic oxidation, based on known methods according to Swedish patents 99019474-7 (tbd) and 0001202-1 (P1158). However, this oxidation method was not proposed to function in the crystalline range in the said patents. Applying the method to function in the crystalline range is proposed in WO2005055860. However, the Swedish patents 99019474-7, 0001202-1 as well as WO 2005055860 disclose a method used in order to obtain a porous and roughened surface. Reference is also made to JP 2000116673 and JP 11033106 relating to a bone implant material which can be used in the crystalline range. Formation and morphologies of thick oxide layers on titanium implants produced by electrochemical oxidation processes are further described in WO 00/72776 A1 and WO 00/72777 A1.

WO 01/76653 A1 describes implants with implant surfaces that were modified by an electrochemical oxidation process such that they possess continuously changing surface characteristics, for example, surface finishing, roughness and/or porosity along the implant dimensions.

SUMMARY

The present invention seeks to provide a dental implant configured to be inserted in a hole in jaw bone that exhibits superior tissue integration properties, soft-tissue seal formation and at the same time a reduced risk of post-implantation complications, in particular arising from deleterious biofilm formation.

The present invention further strives to provide a dental implant configured to be inserted in a hole in jaw bone that once implanted, enables easier and better cleaning of parts of the implant in particular those adjacent to soft tissue, exposed to the peri-implant crevicular fluid (PICF) environment and prone to deleterious biofilm formation, thereby improving dental prophylaxis, oral hygiene and gingival health.

In addition, a dental implant is provided that can specifically prevent peri-implantitis and accommodates the strong demand for a higher predictability of success and long lasting survival rates of dental implants.

The above problems are solved and the objectives achieved by the dental implant according to claim 1. Further embodiments of the dental implant according to claim 1 are described in the respective dependent claims 2 to 14.

The terminology used in the following description is not intended to be limiting the invention. Further, the drawing presented below is an exemplary non-limiting schematic drawing.

The dental implant according to the present invention is configured to be inserted in a hole in jaw bone and to be at least partially situated in the bone tissue when implanted and comprises: a coronal region, an apical region, a longitudinal axis extending from the coronal region of the dental implant to the apical region of the dental implant; an implant surface configured to form an interface between an implant material and the oral environment/surrounding tissue and a surface layer formed on at least part of said implant surface, said surface layer comprising crystalline titanium oxide in the anatase phase and wherein the surface area roughness Sa and the pore size of the implant surface layer is formed increase from the coronal region toward the apical region of the dental implant along the longitudinal axis.

The expression "dental implant" is to be construed widely as an entity that is configured to be used in human or animal dentistry. Furthermore, the dental implant according to this invention is configured to be placed at least partially inside a hole formed in jaw bone in order to provide foundation for further implant constituents that are placed and/or fixed thereon. As a non-exclusive example, the dental implant of the present invention may be a threaded artificial dental root that can threadly engage with the jaw bone and extends from the hard bone tissue into the soft tissue, referred to as "dental screw" in the following. For the sake of intelligibility and purely for illustrative purposes, the following explanations will occasionally employ a "dental screw" as an example of the dental implant, but this does in no way imply that the dental implant according to the present invention is limited thereto. Non-threaded implants, for instance, are within the scope of the invention. Also within the scope of the invention are multi-part dental implants that are assembled by several individual physical entities.

The dental implant further exhibits said longitudinal axis that in case of a dental screw or pin-shaped, substantially cylindrical implant can be a central symmetry axis, e.g., the shaft axis of the dental screw extending along the major axis (length axis) of the dental implant, along which the coronal and apical region are situated. Assuming that the dental implant has an aspect ratio corresponding to its length being distinguishably larger than its width (diameter), then the longitudinal axis is the length axis. The expressions "coronal" and "apical" as well as all other similar terminology found in this application are to be construed in line with the usual meaning they possess in the context of dentistry. Hence, the coronal region of the dental implant is in-situ located where normally the crown region of a tooth at the site of implantation would be situated and the apical region of the dental implant is spaced away from said coronal region in the direction towards the jaw bone and is located where the root region of a tooth at the site of implantation would be situated. Furthermore, the so described coronal and apical regions are to be construed as indicating a "starting point" and an "end point" respectively for the evolution of the below further specified implant surface characteristics (roughness, pore size).

The implant surface basically forms a transitional interface between the material associated to the implant, for example, the implant base/bulk material or an implant coating and in the widest sense the oral environment. The oral environment can comprise particular tissues like mucosal/gingival soft tissue or various types of bone tissue, but is not limited to a particular type. The interface can also be between the implant and the PICF, i.e., so as to basically be an interface between the implant and any conceivable physiological substance encountered in the PICF, for example, the saliva or serum. The environment encountered depends on where the coronal region/part of the implant is located after implantation, for example, submerged, flush and protruded. The terminology "implant surface" preferably refers to outer surfaces of the implant, which as explained above, delimit the implant relative to the environment.

The surface layer of the dental implant is formed on at least part of the implant surface, which includes the options that either only one distinct region of the implant surface or a plurality of regions have the surface layer formed thereon or that even the entire implant surface is fully covered with said surface layer. The general nature of said surface layer is also not particularly limited, however "formed" is to be construed such that the surface layer is a non-native/artificial layer that was purposefully and deliberately formed on the implant surface. Conceivable are layers that are formed by conversion of implant surface material, for example, via phase transitions or reactions on the implant surface. Such layer types do normally not involve the application of additional material on the implant surface and originate instead inherently, from the implant base material itself being converted/transformed by means of any of the known procedures. Other conceivable types of layers comprise layers applied to the implant surface via coating processes, in which conventionally, additional material is applied to a largely unchanged/native implant surface. The surface layer of the present invention comprises crystalline titanium oxide in the anatase phase, which means that at least part of said surface layer exhibits anatase.

The implant surface is characterized in that the surface area roughness Sa and the pore size increase from the coronal region toward the apical region of the dental implant, basically along the longitudinal axis. This feature can also be so understood that the implant surface on which the surface layer is formed possesses a gradient in roughness and pore size along the longitudinal axis. Hence, both surface characteristics increase as observed along the longitudinal axis from the coronal end (region) to the apical end. The surface roughness Sa and the pore size can preferably be minimal in the coronal region and increase towards the apical region, preferably becoming maximal there. The coronal region would hence be distinguished by a flat, smooth surface with voids (pores) with small pore sizes, whereas in the apical region the surface would be pronouncedly uneven with voids with larger pore sizes. Preferably, the pore size is the average pore diameter calculated from the measured pore area and assuming a circular shape. An increase in pore size along the longitudinal axis towards the apical region would then be mainly caused by average pore size changes from pores with small diameters in the coronal area to pores with significant larger diameters in the apical region.

The above defined dental implant possesses a number of technical advantages and realizes a particular beneficial combination thereof. Firstly, the configuration of the apical region that is to be anchored in the jaw bone of having a comparatively rough and porous anatase surface strongly promotes osseointegration. The apical implant surface is highly biocompatible and chemically and structurally well suited for bone tissue to adhere and grow into such that the implant becomes well anchored within the bone and can bear the significant loads imparted thereon. The requirements for the coronal region are distinctively different. Here, the implant surface may be exposed to the PICF and its biochemical environment and also marks the transition to soft tissue. It is desired that a strong soft tissue seal is formed and preserved and further that exposed regions of the implant surface do not exhibit pronounced biofilm formation that may then lead to the above complications. It was found by the inventors that the limited bacteria growth observed for conventional smooth machined implant surfaces can be enhanced further by adding crystalline titanium oxide layers in the anatase phase to said surfaces. In fact, for titanium implants, studies revealed that the adherence of certain types of bacteria to said implant surface with the surface layer formed thereon was significantly reduced as compared to native machined implant surfaces. Therefore, microbial colonization and biofilm formation can be reduced and good tissue sealing preserved. In addition, the smooth surface of the dental implant with the surface layer formed thereon also allows for easier cleaning in the coronal region and biofilm formation can be further reduced and countered. The dental implant exhibits pronounced synergistic effects in that the specifically designed implant surface reduces biofilm formation and establishes strong tissue sealing in the coronal region, which in turn positively effects the integration of the implant in the jaw tissues, since a potentially problematic microbial source is largely avoided and inflammatory processes or infections effecting tissue integration at the coronal level are suppressed. As a result, a dental implant is obtained that in sum has overall improved survival rates and compatibility. As regards the spatial extent of the coronal and the apical regions it follows that the regions have to be provided such that the above advantages can be realized. In other words, implant regions to be situated and integrated into bone tissue should exhibit the above properties of the apical region. It would not make sense to construe the invention such that the coronal region may also extend down to the apical tip of the dental implant and into the bone, where in fact good anchorage is required. On the other hand, it is technically also not sensible to construe the present invention such that the apical region extends all the way to the coronal region of the implant, since this would undermine the objective of providing reduced surface roughness, reduced biofilm formation and good cleaning conditions.

In the following paragraphs, preferred embodiments of the present invention according to the dependent claims will be described. Consequently, the following preferred embodiments advance the above described dental implant further and are also freely combinable amongst each other.

In a preferred dental implant, the surface area roughness $S_a$ of the implant surface on which said surface layer is formed increases along the longitudinal axis from a value of 0.1, preferably 0.2 µm in the coronal region of the dental implant to a value of at least 1 µm in the apical region of the dental implant, and an average pore size of pores intersecting the implant surface on which said surface layer is formed increases along the longitudinal axis from a value of <0.1 µm in the coronal region of the dental implant to a value of at least 1 µm in the apical region of the dental implant.

For the above preferred dental implant, desired surface features are further specified and it can be seen that the coronal region may be characterized by a low surface roughness and pores with comparatively small average pore dimensions. In contrast, towards the apical region, the surface morphology changes in that the average pore sizes increase significantly. As a result, all the above described technical effects are further promoted in an unexpected degree, by the specifically designed surface of this preferred implant. The average pore size at the coronal region shall preferably be so small that bacteria cannot enter into them, typically <0.2 µm. Furthermore the presence of anatase in the layer at the coronal section may reduce the bacteria adhesion.

It is further preferred that the surface area roughness $S_a$ and/or the pore size of the implant surface on which said surface layer is formed increase continuously along the longitudinal axis from the coronal region to the apical region. In other words, it is preferred that the increase in roughness and pore size occurs so along the longitudinal axis in the direction towards the apical end that no distinct transitions or "steps" exist, but instead the implant surface regions merge and blend smoothly. This increases the in-use flexibility of the dental implant, since no spatially discrete step change in implant surface characteristics occurs, which would require a more precise implantation.

In a further preferred dental implant, the implant surface on which said surface layer is formed comprises a transitional region between the coronal region and the apical region of the dental implant. The area surface roughness $S_a$ of the implant surface on which said surface layer is formed in the coronal region of the dental implant is in the range of 0.1, preferably 0.2 µm to 0.5 µm and an average pore size of pores intersecting the implant surface on which said surface layer is formed is minimal with respect to the overall implant surface on which said surface layer is formed, and the area surface roughness $S_a$ of the implant surface on which said surface layer is formed at said transitional region is in the range of 0.5 to 1.0 µm, and further the area surface roughness $S_a$ of the implant surface on which said surface layer is formed in the apical region of the dental implant is in the range of 1.0 to 5 µm and an average pore size of pores intersecting the implant surface on which said surface layer is formed is maximal with respect to the overall coated surface. In the transitional region, these surface properties thus transition from those in the coronal region to those in the apical region. It is preferred that the transitional region touches and is contiguous with the coronal region and/or with the apical region.

The above configuration of the dental implant is distinguished by a transitional region and a specific constitution of the implant surface, basically a three-region design. Firstly, the surface area roughness $S_a$ possesses a comparatively small value in the coronal region and the average pore size at the same is minimal, i.e., is the lowest to be found on the entire implant surface on which said surface layer is formed. This so configured coronal region may then be followed in a direction towards the apical end along the longitudinal axis by said transitional region with an increasing surface area roughness $S_a$. This transitional region may then in turn be followed by a region in the apical region with a yet again increased surface area roughness $S_a$ and an average pore size that is maximal, i.e., the largest to be found on the entire implant surface on which said surface layer is formed. The above configuration confers to the dental implant flexibility in its surface design, wherein the smooth and dense surface in the coronal region and the rough and open surface in the apical region are somewhat fixed, but the transition between these two extremes can be customized via the transitional region, i.e., its position and extent along the longitudinal axis. The implant surface can hence be adapted to specific dental indications and needs of particular patient groups. For example, the transitional region can be so placed and designed that it covers implant regions that are expected/prone to be exposed to soft tissue and PICF due to bone resorption and atrophy. Hence, the exposed regions will experience reduced biofilm formation.

In another preferred dental implant, the crystalline titanium oxide comprised in said surface layer comprises predominantly anatase in the range of 70-100% (phase fraction), and the remainder of the layer comprises rutile, brookite, and amorphous titanium oxide; and/or said implant surface on which said surface layer is formed comprises phosphorus, preferably in the form of phosphates; and/or said implant surface on which said surface layer is formed is combined with at least one of a bone-growth-initiating substance and a bone-growth-stimulating substance, preferably of the superfamily TGF-beta; and/or said implant surface on which said surface layer is formed has an anti-bacterial effect.

The above preferred dental implant defines a number of options for designing the implant surface that could either all be freely combined or employed individually. One option is that the surface layer comprises predominantly titanium oxide ($TiO_2$) predominantly in the anatase modification/phase/form. The preferred anatase fraction contributes to the good osseointegration of the implant in general and promotes the above described desired effects, like, reduced biofilm formation in the coronal region and pronounced bone tissue integration in the apical region. Optionally having phosphorous, preferably in the form of phosphates, in the implant surface on which the surface layer is formed enhances the above beneficial effects of the anatase containing implant surface. It is conceivable that the presence of phosphorous, which is also a constituent of bone apatite, further stimulates bone tissue integration of the dental implant, in particular in the apical region. Similar considerations do apply to the option of having bone-growth-initiating substance and/or a bone-growth-stimulating substance comprised in the surface layer. Here, bone tissue integration can be purposefully and actively improved by stimulating bone cell proliferation and in-growth. A final option is to confer the implant surface an anti-bacterial effect, this can be done, for example, by adding noble metal ions such as silver to the surface, copper (Cu), and/or any agent with known antimicrobial effect towards the oral cavity bioflora. In particular, in the coronal region of the dental implant such anti-bacterial effect can further promote the suppression of biofilm formation and microbial colonization. The possible ways and permutations in which the above options are realized are not limited. Depending on the desired functionalities along, for example, the longitudinal axis of the dental implant, the above options can spatially be freely and purposefully combined or omitted.

The overall constitution of the surface layer formed on the implant surface can be described as consisting of 1) titanium oxide, which in turn is preferably composed as above with anatase being the predominate titania phase and further 2) optionally at least one of the above constituents, namely: phosphorous/phosphates, a bone-growth-initiating substance and/or a bone-growth-stimulating substance and an antibacterial agent.

In a further preferred dental implant the surface layer formed on at least part of said implant surface has a thickness between 50 and 500 nm in the coronal region, an between 1 and 20 μm in the apical region. The preferred layer thickness is purposefully chosen according to the main functionality intended for said implant parts. A larger layer thickness in the apical region ensures that there is enough material to form the rough and open-structures on the implant surface with high porosity. In case bone tissue integration also relies on resorption of the surface layer during the integration process, it is also ensured that enough material for that is provided. A thinner surface layer in the coronal region can be beneficial in that it masks the underlying native implant surface less and its potentially beneficial structure is still effective at the implant surface. This is in particular applicable for dental implants with conventionally machined surfaces, which will be further described below. The manner in which the different layers thicknesses are realized is not particularly limited. Conceivable is a continuous thickness gradient along the longitudinal direction of the dental implant, but distinct steps in layer thickness are also possible. The dental implant can hence, in addition to increasing roughness and pore size, also possess an increasing surface layer thickness, which increases from the coronal to the apical region along the longitudinally axis and is optionally lowest in the coronal and largest in the apical region In yet another preferred dental implant, the implant surface of the dental implant is fully covered with said surface layer from the coronal to the apical region and vice versa, such that none of the implant surface remains uncovered. This particular dental implant is intended not to have an implant surface in which the native implant base/bulk material is exposed to the oral environment/tissue. The implant is fully covered with the surface layer, particularly also in a machined collar region of the implant, which conventionally is often left uncoated/uncovered. Here, an "all-the-way-up" (AWU) or "all-the-way-down" (AWD) design is realized, wherein the surface layer extends all the way to the (coronal) top and (apical) bottom of the dental implant. An AWU layer with surface roughness >1 μm is preferred in cases where the entire implant is embedded in bone, and an AWD layer with surface rougness <0.2 μm is preferred in cases where a large section of the implant is exposed to soft tissue.

In an additional preferred dental implant, the implant surface is at least partially a machined surface and/or further a region of the implant surface in the coronal region of the dental implant is machined and is at least partially so configured that the characteristics of the implant surface as-formed by said machining are maintained/preserved when the surface layer is superimposed. As "machined surface", surfaces of dental implants are meant that result from machining like turning and milling. In particular, in case the dental implant is a dental screw, then the thread is conventionally produced by turning and the collar region may additionally be machined with by high precision/quality turning or grinding. Such machined surfaces are considered a gold-standard for soft tissue integration, since they have found to yield good soft tissue integration. Hence, it may be desirable to preserve the characteristics, for example, surface roughness and roughness profile of said machined surface and combine them with the beneficial effects of a crystalline anatase surface layer. In fact, the inventors found that a particularly high performance with respect to the suppression of microbial colonization and biofilm formation can be achieved if the machined surface is covered with a thin crystalline, anatase-comprising surface layer, when the underlying structure of the machined surface is not canceled out (fully masked) by the layer on top.

In the above region, where the machined surface characteristics are maintained, it is further preferred that the area surface roughness Sa is in the range of 0.1 to 0.5 μm and an average pore size of pores intersecting the implant surface on which said surface layer is formed is <0.1 μm, thereby further enhancing the above described effect.

In addition, it may be preferred that the implant surface is at least partially a rolled surface. In particular in cases where the dental implant is a dental screw, the screw thread may not be produced by turning or cutting, but instead by a rolling process. The latter process is different with respect to its impact on the implant surface. Rolling may in fact result in locally more varying degrees of deformation and densification along the implant surface, which in turn can affect the characteristics of the surface layer to be formed and the biological response to such a dental implant. It is also within the scope of the present invention that at least the above two techniques are combined, for example, wherein a thread is largely produced by rolling, but certain parts of the implant, for instance the neck, are (surface-) finished by machining methods.

In another preferred dental implant, the implant material comprises or consists of titanium or a titanium alloy. With other words, the dental implant's base/bulk material at least comprises titanium or a titanium alloy, but may also be formed completely of said materials. Titanium and titanium-based materials have been proven ideal materials for all types of implants and combine high biocompatibility with superior mechanical and chemical (corrosion) properties. These advantages are also employed for the present invention in order to have a reliably and durable underlying basis for designing the implant's surface properties. Titanium materials as base materials are also particularly suited for generating the desired crystalline anatase surface layer therefrom.

For a dental implant as above comprising titanium, the surface layer is generated by an anodic oxidation process, in part. Said process is employed as in the below referenced publications and is an electrochemical method that leads to the oxidation of the implant base/bulk material such that a transformation surface layer is formed. The anodic oxidation processes a high flexibility and very versatile surface morphologies can be generated ranging from thin, smooth crystalline oxide surfaces with low porosity to thick, rough and highly porous layers as to be found on the surface of the dental implant according to the present invention.

BRIEF DESCRIPTION OF THE DRAWINGS

The various aspects, features and advantages of the present invention will further become apparent from the following description of ways of carrying out the invention in combination with the following accompanying drawing, in which:

FIG. 1 is a schematic drawing of a screw-like dental implant with an illustration of surface morphologies encountered on the implant's surface along its longitudinal axis.

DETAILED DESCRIPTION

Specific ways of carrying out the invention will now be described in detail, where appropriate with reference to the accompanying drawing. The specific embodiments are not intended to unduly limit the invention, but are rather provided so that the disclosure will be thorough, complete and will fully convey the scope of the invention to the skilled person.

One way of putting the present invention into practice is shown in FIG. 1 appended to this application. Therein, a screw-like dental implant 1 is depicted. As described earlier, said screw is to be considered a mere illustrative example of a dental implant according to the present invention for the sake of comprehensibility, but not as being construed limiting. In FIG. 1 the dental implant 1 is a somewhat conical screw with an outer thread for engaging with bone tissue and a longitudinal axis L, running as a rotational axis of the cone-like implant from its coronal region indicated by the bracket 2 to the implant's apical region as indicated by bracket 3. The actual extent of these regions is not meant to be ultimately defined by the brackets 2 and 3, which are mainly illustrational. However, what the size of the brackets and their positions may however indicate is that the coronal and apical regions are not necessarily meant to be directly adjacent to each other. It is hence conceivable that both regions are "separated" along the longitudinal axis L by a transitional region 4. The implant's surface is indicated by reference numeral 5 and for the sake of intelligibility said surface in region 2 is illustrated on the one hand by a metallic-like surface (upper half of coronal region 2) and a grey-shaded/structured region below, extending all the way down to the apical region 3. The latter is meant to represent the implant surface on which at least partially a surface layer is formed. Here "partially" means that the uppermost (coronal) part of the implant is as-machined, i.e., as described above is a finished metal surface. However, it is also within the scope of the invention that the surface layer extends all the way up and that hence such metallic surface without surface layer does no longer exist. The implant surface with the surface layer formed thereon is illustrated by the grey, structured and dully-drawn parts of the screw. This should indicate the titanium oxide containing surface layer formed on the implant's surface. Specifically here, the surface layer comprises anatase and phosphates. The insets (a) to (d) are actual electron micrographs taken at different positions of the implant surface 5 along the axis L and illustrate the morphological evolution along the implant surface 5 with the surface layer formed thereon. Inset (a) basically shows a morphological "starting point" in the coronal region 2 with little electron contrast and image features. The corresponding region of the implant is characterized by an as-machined, for example, metallic surface in which a comparatively thin, smooth and dense titanium oxide layer, predominantly comprising anatase is formed. Surface roughness measurements in said region yield a low roughness of Ra 0.2 μm. When "moving" further along the axis L towards the apical region 3 of the dental implant 1, observable and measurable changes occur. Inset (b) already indicates a certain "waviness" of the surface, which is reflected by a higher roughness of Ra 0.5 μm. At the same time, pores appear as black, low image signal yield regions in the electron micrograph. Insets (c) and (d) then first and foremost document that the waviness transforms somewhat in an "island"-structure and the roughness measured increases accordingly from Ra 0.8 μm to Ra 1.5 μm. Inset (d) in particular shows that in the apical region 3 an morphological "end point" is reached, where roughness, pore size and layer thickness reach a maximum, starting from the coronal region 2 with the corresponding minimum. Although the morphological evolution has above been documented by roughness values Ra, the same observations do apply for the related roughness value Sa. The transition between the two extremes can occur gradually and continuously throughout the transitional region 4 along the axis L as insets (b) and (c) show. It is understandable from insets (a) and (d) that the first shows a surface optimal with respect to ease of cleaning and provides only few sites/pockets/retreats for colonization with bacteria, whereas the latter shows a surface that is obviously predestined for bone tissue to embrace the island-structure and to grow into the open pores on the implant surface establishing a solid mechanical link to the implant. This advantageous structural functionality of the implant surface documented by micrographs and surface measurements consorts with a (bio-) chemical functionality that results from titanium oxide being beneficial for osseointegration and as argued above, also for the suppression of biofilm formation.

The surface characteristics employed to qualify the properties of the implant surface with the surface layer, surface area roughness Sa and pore size, are to be construed as having the meaning the person skilled in the art of surface science and metrology would allocate them.

Mean roughness (Sa) is measured at points covering 630×470 μm using a WYKO NT9100 optical profiling system. Data are evaluated in WYKO software Vision 4.10, which provides data processing by extrapolation of "dead pixels", tilt correction and smoothing with a 5×5 median filter. With respect to the surface roughness, it should be understood that the surface of the implant on which said surface layer is formed is actually caused by the superposition of individual roughness components. On the one hand, the original/native implant surface will possess an inherent roughness that is largely determined by the way the bulk implant itself is manufactured and its surface finished. For dental implants, machined implant surfaces are showing good osseointegration and soft tissue integration performance. On the other hand, the surface layer formed at least partially on said implant surface also possesses an inherent roughness. Consequently, the overall surface roughness could be considered, for example, as a superposition of a microscale amplitude, low frequency roughness of an as-machined/finished implant surface and a nanoscale amplitude, high frequency roughness of the surface layer formed thereon.

The porosity of the implant surface in the present application is preferably an "open porosity", which means only voids that are superficially detectable, i.e., that are intersected by the implant surface plane(s) are taken into account. Pores or voids formed in the bulk of the implant material or inside the surface layer, but not extending to and intersecting the implant surface do not contribute to the porosity of the implant surface. Said latter porosity itself is further determined by the pore size thereof. The porosity can generally be determined as the fraction of a surface area formed by voids with respect to the surface area formed by material. The skilled person would readily choose a well-known standard method and apparatus to measure said porosity. A widely used method for determining the porosity of surfaces, as it is desired in the present invention, is image analysis of micrographs taken from the surfaces in question. This method is based on image signal differences between pores on the surface and surface regions with material. The first generally having low signal yield and often appear black in corresponding micrographs. Modern image analysis techniques can then evaluate the fraction of these low contrast regions per image and therefrom, the porosity can be deduced. Said micrographs can, depending on the pore size, be recorded via (reflected-) light microscopy or electron microscopy, wherein the image analysis procedures are basically identical for either method. The pore size is determined by simply measuring the size of individual pores directly in the micrographs, which can be done electronically with software tools incorporated in conventional image analysis software. In addition to the above method, it is also conceivable to determine the surface roughness and porosity via tactile or non-tactile scanning methods that are capable of yielding three dimensional surface information on the required scale, for example, AFM, interference or laser-scanning techniques.

As regards ways of generating the above described implant surface, reference is made to the methods of modifying an implant's surface in the publications WO 00/72777 A1 and Wo 01/76653 A1, which were also employed to produce the dental implant according to the present invention, in particular, these dental implants comprising or consisting of titanium or a titanium alloy.

Scale indicated in inset (a) is 2 μm.
Scale indicated in inset (b) is 10 μm.

The invention claimed is:

1. A method of placing a dental implant into a patient's jawbone, the method comprising:
    inserting the dental implant into a hole in the patient's jawbone, the dental implant comprising:
        a coronal region;
        an apical region;
        an implant surface;
        a surface layer formed on at least part of said implant surface,
        wherein said implant surface on which said surface layer is formed includes a surface area roughness Sa,
        wherein said surface area roughness Sa of said implant surface on which said surface layer is formed has a value of at least 0.1 μm in the coronal region of the dental implant and a value of at least 1 μm in the apical region of the dental implant, and
        wherein said surface layer on the implant surface has a thickness such that the surface area roughness Sa of the implant surface at the coronal region is not canceled out by said surface layer;
    at least partially situating the apical region adjacent bone tissue; and
    exposing the coronal region adjacent soft tissue.

2. The method according to claim 1, wherein the surface area roughness Sa of the implant surface on which said surface layer is formed in the coronal region of the dental implant is in the range of 0.1 μm to 0.5 μm.

3. The method according to claim 1, wherein said surface area roughness Sa of said implant surface on which said surface layer is formed has a value of at least 0.2 μm in the coronal region of the dental implant.

4. The method according to claim 3, wherein the surface area roughness Sa of the implant surface on which said surface layer is formed in the coronal region of the dental implant is in the range of 0.2 μm to 0.5 μm.

5. The method according to claim 1, wherein the surface area roughness Sa of the implant surface on which said surface layer is formed in the apical region of the dental implant is in the range of 1.0 to 5 μm.

6. The method according to claim 1, wherein the surface area roughness Sa of the implant surface on which said surface layer is formed increase from the coronal region to the apical region.

7. The method according to claim 1, wherein said implant surface on which said surface layer is formed includes a pore size, and wherein an average pore size of pores intersecting the implant surface on which said surface layer is formed has a value of <0.2 μm in the coronal region of the dental implant.

8. The method according to claim 7, wherein the average pore size of pores intersecting the implant surface on which said surface layer is formed has a value of <0.1 μm in the coronal region of the dental implant.

9. The method according to claim 1, wherein said implant surface on which said surface layer is formed includes a pore size, and wherein an average pore size of pores intersecting the implant surface on which said surface layer is formed is minimal in the coronal region with respect to the overall implant surface on which said surface layer is formed.

10. The method according to claim 1, wherein said implant surface on which said surface layer is formed includes a pore size, and wherein an average pore size of pores intersecting the implant surface on which said surface layer is formed has a value of at least 1 µm in the apical region of the dental implant.

11. The method according to claim 1, wherein said implant surface on which said surface layer is formed includes a pore size, and an average pore size of pores intersecting the implant surface on which said surface layer is formed is maximal in the apical region with respect to the overall implant surface.

12. The method according to claim 1, wherein said implant surface on which said surface layer is formed includes a pore size, and wherein the pore size of the implant surface on which said surface layer is formed increase from the coronal region to the apical region.

13. The method according to claim 1, wherein said surface layer is thicker in the apical region than in the coronal region, wherein said surface layer has a thickness between 50 and 500 nm in the coronal region.

14. The method according to claim 1, wherein said surface layer at least partially formed on said implant surface has a thickness between 1 and 20 µm in the apical region.

15. The method according to claim 1, wherein the implant material comprises or consists of titanium or a titanium alloy.

16. The method according to claim 1, wherein at least part of said surface layer comprises crystalline titanium oxide in the anatase phase in at least the apical region.

17. The method according to claim 16, wherein the crystalline titanium oxide comprised in said surface layer comprises anatase in the range of 70-100% and wherein the remaining of the layer comprises rutile and/or amorphous titanium oxide.

18. The method according to claim 1, wherein said implant surface on which said surface layer is formed comprises phosphorus.

19. The method according to claim 1, wherein a region of the implant surface in the coronal region of the dental implant is machined and at least partially so configured that the characteristics of the implant surface as-formed by said machining are maintained when the surface layer is superimposed.

20. The method according to claim 1, wherein the implant surface is at least partially a rolled surface.

* * * * *